US00PP15873P2

(12) United States Plant Patent
van Rijn

(10) Patent No.: US PP15,873 P2
(45) Date of Patent: Jul. 19, 2005

(54) ***ANTHURIUM* PLANT NAMED 'RIJN200004'**

(50) Latin Name: *Anthurium andreanum*
Varietal Denomination: Rijn200004

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 10/766,775

(22) Filed: Jan. 28, 2004

(51) Int. Cl.[7] ..... A01H 5/00

(52) U.S. Cl. ..... Plt./365

(58) Field of Search ..... Plt./365

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Anthurium* plant named 'Rijn200004', characterized by its upright and outwardly spreading plant habit; freely clumping growth habit; durable dark green leaves; red-colored spathes with whitish-colored spadices that are positioned slightly above and beyond the foliage on strong and erect scapes; freely flowering habit; and good inflorescence longevity.

2 Drawing Sheets

Botanical classification/cultivar designation: *Anthurium andreanum* cultivar Rijn200004.

BACKGROUND OF THE INVENTION

The present invention relates to a new and distinct cultivar of *Anthurium* plant, botanically known as *Anthurium andreanum,* and hereinafter referred to by the name 'Rijn200004'.

The new *Anthurium* is a product of a planned breeding program conducted by the Inventor in Schipluiden, The Netherlands. The objective of the program is to create and develop new compact, freely clumping and freely flowering *Anthurium* cultivars with strong roots, dark green leaves, attractive spathe color, and good inflorescence longevity.

The new *Anthurium* originated from a cross by the Inventor on Feb. 8, 1999 of a proprietary selection of *Anthurium andreanum* identified as code number 9001, not patented, as the female, or seed, parent with a proprietary selection of *Anthurium andreanum* identified as code number 9813, not patented, as the male, or pollen, parent. The cultivar Rijn200004 was discovered and selected by the Inventor as a flowering plant within the progeny of the stated cross in a controlled environment in Schipluiden, The Netherlands on Aug. 23, 2000.

Asexual propagation of the new cultivar by meristem culture in a laboratory in Belgium since August, 2000, has shown that the unique features of this new *Anthurium* plant are stable and reproduced true to type in successive generations of asexual propagation.

BRIEF SUMMARY OF THE INVENTION

The new *Anthurium* has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Rijn200004. These characteristics in combination distinguish 'Rijn200004' as a new and distinct cultivar:

1. Upright and outwardly spreading plant habit.
2. Freely clumping growth habit.
3. Durable dark green-colored leaves.
4. Red-colored spathes with whitish-colored spadices that are positioned slightly above and beyond the foliage on strong and erect scapes.
5. Freely flowering habit.
6. Good inflorescence longevity.

Plants of the new *Anthurium* can be compared to plants of the female parent, the proprietary selection identified as code number 9001. In side-by-side comparisons conducted in Schipluiden, The Netherlands, plants of the new *Anthurium* differed from plants of the selection 9001 in the following characteristics:

1. Plants of the new *Anthurium* had smaller leaves than plants of the selection 9001.
2. Plants of the new *Anthurium* and the selection 9001 differed in spadix coloration.

Plants of the new *Anthurium* can be compared to plants of the male parent, the selection 9813. In side-by-side comparisons conducted in Schipluiden, The Netherlands, plants of the new *Anthurium* differed from plants of the selection 9813 in the following characteristics:

1. Plants of the new *Anthurium* had larger and darker green-colored leaves than plants of the selection 9813.
2. Plants of the new *Anthurium* and the selection 9813 differed in spadix coloration.

Plants of the new *Anthurium* can be compared to plants of the cultivar Red Queen, disclosed in U.S. Plant Pat. No. 11,813. In side-by-side comparisons conducted in Schipluiden, The Netherlands, plants of the new *Anthurium* differed from plants of the cultivar Red Queen in the following characteristics:

1. Plants of the new *Anthurium* had more durable and darker green-colored leaves than plants of the cultivar Red Queen.
2. Plants of the new *Anthurium* and the cultivar Red Queen differed in spathe coloration.

BRIEF DESCRIPTION OF THE PHOTOGRAPHS

The accompanying colored photographs illustrate the overall appearance of the new *Anthurium,* showing the colors as true as it is reasonably possible to obtain in colored reproductions of this type. Colors in the photographs may differ slightly from the color values cited in the detailed botanical description which accurately describe the colors of the new *Anthurium*.

The photograph on the first sheet comprises a side perspective view of a typical flowering plant of the cultivar Rijn200004.

The photograph at the top of the second sheet comprises a close-up view of typical inflorescences of 'Rijn200004'.

The photograph at the bottom of the second sheet comprises a close up view of developing and fully expanded leaves of 'Rijn200004'.

DETAILED BOTANICAL DESCRIPTION

In the following description, color references are made to The Royal Horticultural Society Colour Chart, 2001 Edition, except where general terms of ordinary dictionary significance are used. The aforementioned photographs and the following observations and measurements describe seven-month old plants grown in 14-cm containers in Schipluiden, The Netherlands, in a glass-covered greenhouse with average day temperatures of 23° C., average night temperatures of 21° C. and light levels about 6 kilolux.

Botanical classification: *Anthurium andreanum* cultivar Rijn200004.

Parentage:

*Female parent.*—Proprietary selection of *Anthurium andreanum* identified as code number 9001, not patented.

*Male parent.*—Proprietary selection of *Anthurium andreanum* identified as code number 9813, not patented.

Propagation:

*Method.*—By meristem culture.

*Time to initiate roots on a meristem-cultured plant.*—About four weeks at 20 to 24° C.

*Time to develop roots on a meristem-cultured plant.*—About nine months at 20 to 24° C.

*Root description.*—Thick, fleshy, dark pink to cream-colored; lateral roots, thick and abundant.

Plant description:

*Plant shape.*—Upright and outwardly spreading plant habit, broad inverted triangle, symmetrical.

*Growth habit.*—Freely clumping, bushy and dense growth habit; about four clumps per plant; moderately vigorous to vigorous.

*Plant height, from soil level to top of leaf plane.*—About 46 cm.

*Plant height, from soil level to top of inflorescences.*—About 57 cm.

*Plant diameter or spread.*—About 66 cm.

*Foliage description.*—Arrangement: Alternate; simple. Length: About 24.2 cm. Width: About 15 cm. Shape: Narrowly cordate. Apex: Apiculate. Base: Cordate to auriculate. Margin: Entire, slightly undulate. Texture, upper and lower surfaces: Leathery; glabrous, smooth; durable. Venation pattern: Pinnate. Color: Developing leaves, upper surface: More green than 146A. Developing leaves, lower surface: 146A. Fully developed leaves, upper surface: Darker than between 139A and 147A. Fully developed leaves, lower surface: 146A. Venation, upper surface: 138A to 138B. Venation, lower surface: 144A to 144B. Petiole: Length: About 30.9 cm. Diameter, just below geniculum: About 4 mm. Diameter, at plant base: About 7 mm. Texture: Smooth, glabrous. Color: Between 143A and 144A. Geniculum length: About 2.2 cm. Geniculum diameter: About 5 mm. Geniculum color: Between 143B and 144A to 144B. Wing length: About 2 cm. Wing diameter: About 4 mm. Wing color: 141A to 143B.

Inflorescence description:

*Inflorescence arrangement.*—Spathes with spadices held slightly above and beyond the foliage. Flowering structures arise from leaf axils. Freely and continuous flowering during the autumn in Schipluiden, The Netherlands. Typically about seven inflorescences per plant. Inflorescences not fragrant.

*Inflorescence longevity.*—Inflorescences last about two months under winter conditions and about three months under summer conditions; inflorescences persistent.

*Spathe.*—Length: About 11.3 cm. Width: About 9.5 cm. Shape: Cordate. Apex: Abruptly acute, reflexed. Base: Cordate. Margin: Entire, undulate. Texture, upper and lower surfaces: Leathery; glabrous, smooth. Surface, upper and lower surfaces: Rugose. Color: When developing, front surface: 46C, towards the basal margins, 45C. When developing, rear surface: 47C to 47D. Fully developed, front surface: 46B to 46C, towards the basal margins, 46C; color becoming closer to N34A, towards the basal margins, 144A, with development. Fully opened, rear surface: 47D.

*Spadix.*—Length: About 6 cm. Diameter: About 8 mm. Shape: Columnar, tapering towards the apex; apex, obtuse. Cross section: Rounded. Aspect: About 10° from vertical. Color: Immature: 34A; towards the apex, 154B to 154C. Mature: 37C to 37D to 179D; towards the apex, 48C to 48D.

*Flowers.*—Quantity per spadix: Numerous, about 300. Shape: Rounded. Height: About 0.5 mm. Diameter: About 0.8 mm.

*Reproductive organs.*—Androecium: Anther color: 11D. Amount of pollen: Moderate. Pollen color: 11C. Gynoecium: Stigma shape: Ovoid. Stigma color: N155B. Ovary color: N155B.

*Scape.*—Length: About 38.9 cm. Diameter: About 5 mm. Strength: Strong. Aspect: Erect to slightly outwardly slanted to about 20° from vertical. Color: Between 146A.

*Seed and fruit.*—Seed and fruit development has not been observed on plants of the new *Anthurium*.

Disease/pest resistance: Under commercial production conditions, plants of the new *Anthurium* have not been observed to be resistant to pathogens or pests common to *Anthurium*.

Temperature tolerance: Plants of the new *Anthurium* have been observed to tolerate temperatures from about 14 to 36° C.

It is claimed:

1. A new and distinct cultivar of *Anthurium* plant named 'Rijn200004', as illustrated and described.

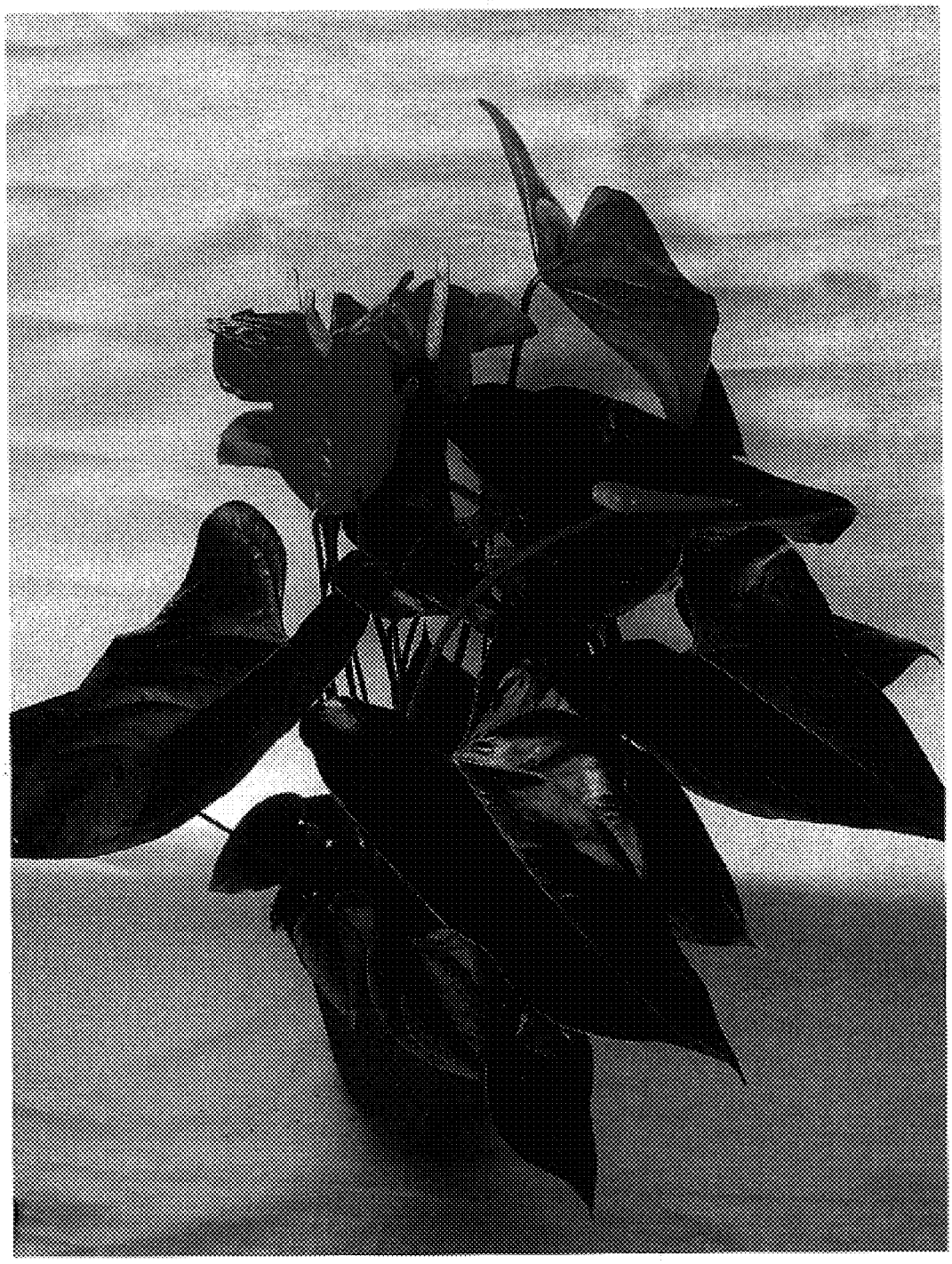

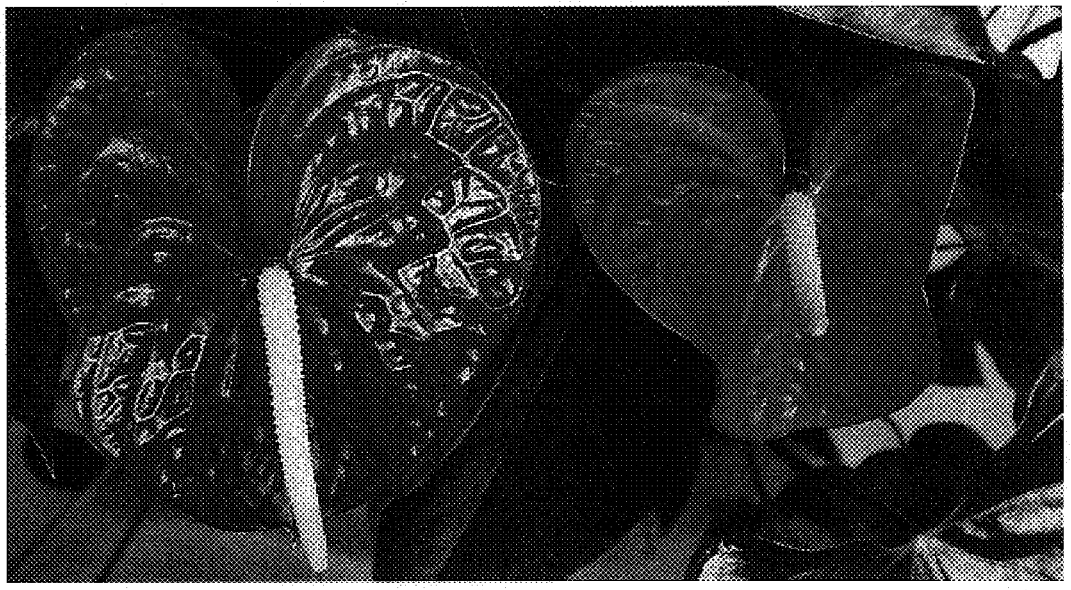
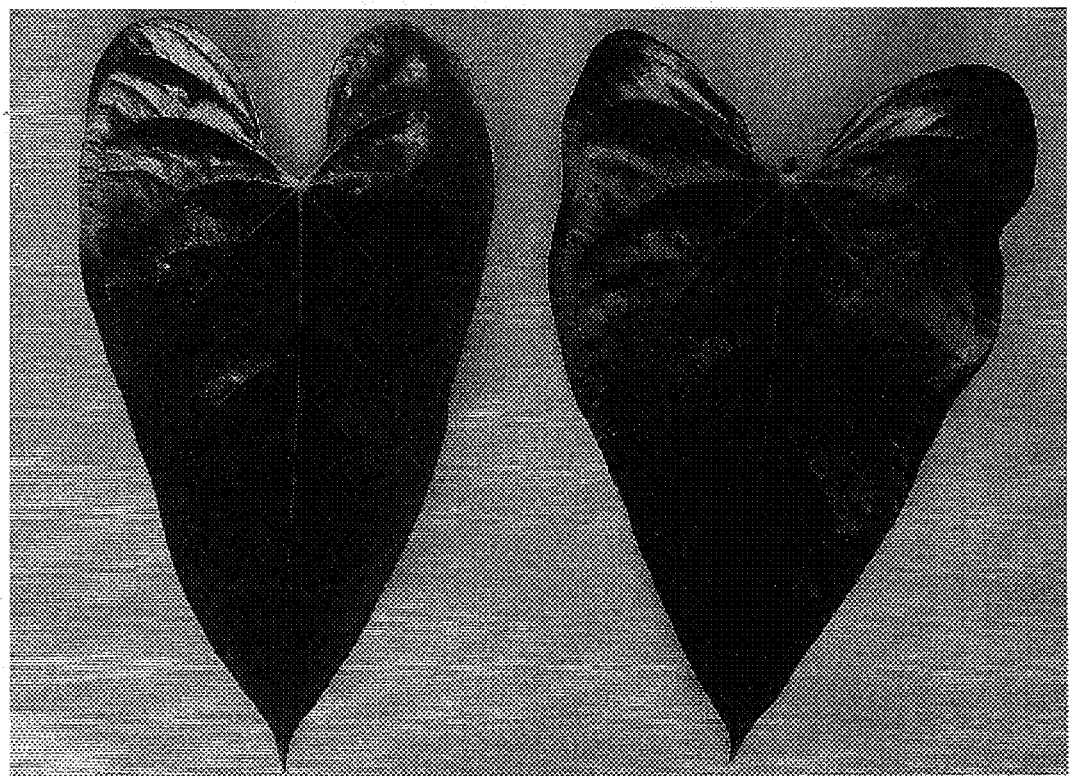

* * * * *